(12) United States Patent
Okamoto et al.

(10) Patent No.: US 10,520,466 B2
(45) Date of Patent: Dec. 31, 2019

(54) GAS SENSOR

(71) Applicant: NGK INSULATORS, LTD., Nagoya-shi, Aichi (JP)

(72) Inventors: Taku Okamoto, Nagoya (JP); Yuki Nakayama, Nagoya (JP); Noriko Hirata, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 165 days.

(21) Appl. No.: 15/708,431

(22) Filed: Sep. 19, 2017

(65) Prior Publication Data

US 2018/0088074 A1    Mar. 29, 2018

(30) Foreign Application Priority Data

Sep. 23, 2016   (JP) ................................ 2016-185161

(51) Int. Cl.
  *G01N 27/406* (2006.01)
  *G01N 27/407* (2006.01)
(52) U.S. Cl.
  CPC ..... *G01N 27/4077* (2013.01); *G01N 27/4071* (2013.01); *G01N 27/4075* (2013.01); *G01N 27/4076* (2013.01)
(58) Field of Classification Search
  CPC .......................................... G01N 27/406–4118
  See application file for complete search history.

(56) References Cited

U.S. PATENT DOCUMENTS

| 5,194,135 A | * | 3/1993 | Hayakawa | ........... G01N 27/417 204/425 |
| 5,935,399 A | * | 8/1999 | Tanaka | ............... G01N 27/4075 204/424 |
| 6,325,906 B1 | * | 12/2001 | Kitanoya | ............. G01N 27/419 204/425 |
| 8,133,370 B2 | | 3/2012 | Roessler et al. | |
| 2015/0293051 A1 | * | 10/2015 | Kajiyama | .......... G01N 27/4075 204/424 |
| 2016/0033447 A1 | | 2/2016 | Nakasone et al. | |

FOREIGN PATENT DOCUMENTS

| JP | 4914447 B2 | 4/2012 |
| JP | 2012-211928 A | 11/2012 |
| JP | 5883976 B2 | 3/2016 |

* cited by examiner

*Primary Examiner* — Bach T Dinh
(74) *Attorney, Agent, or Firm* — Mattingly & Malur, PC

(57) ABSTRACT

A gas sensor that is unlikely to have Au evaporation from an external electrode even when used under a high temperature atmosphere is provided. The gas sensor includes a sensor element mainly made of an oxygen-ion conductive solid electrolyte; an external electrode provided on the sensor element and containing a Pt—Au alloy; and an electrode evaporation preventing film provided on the sensor element while being insulated from the sensor element and separated from the external electrode, and made of Au or a Pt—Au alloy having an Au composition ratio not smaller than an Au composition ratio of the Pt—Au alloy contained in the external electrode. A protection cover is provided so that at least part of the sensor element, at which the external electrode and the electrode evaporation preventing film is positioned, is inside the protection cover, and so that a measurement gas is introduced inside the protection cover.

10 Claims, 10 Drawing Sheets

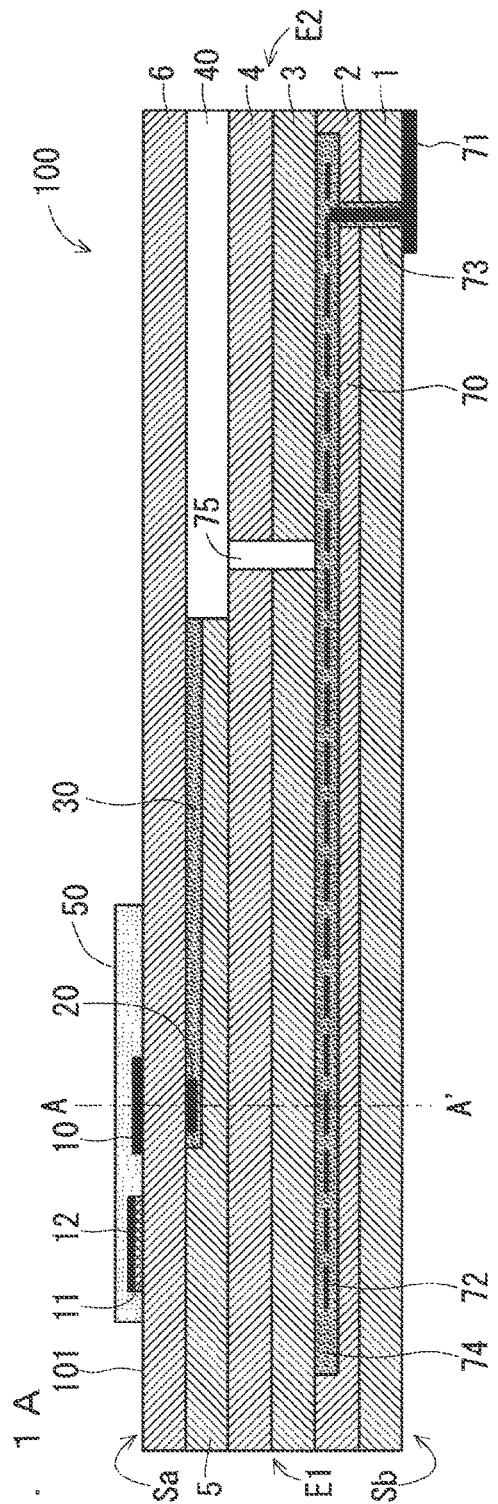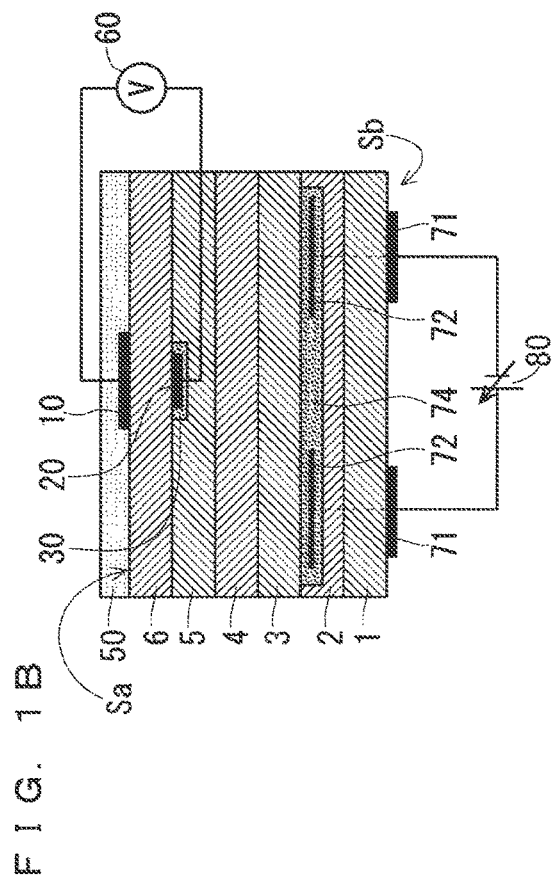
FIG. 1A
FIG. 1B

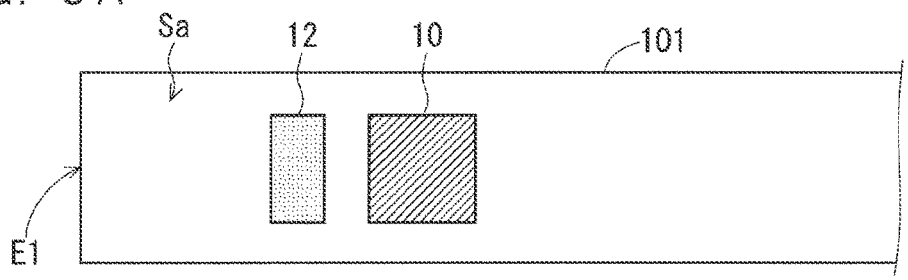
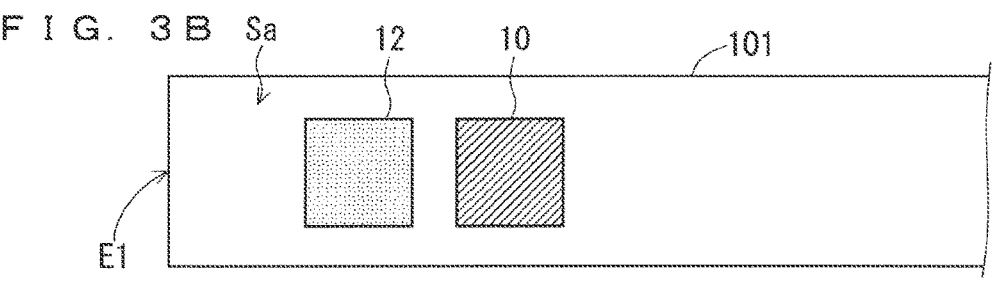
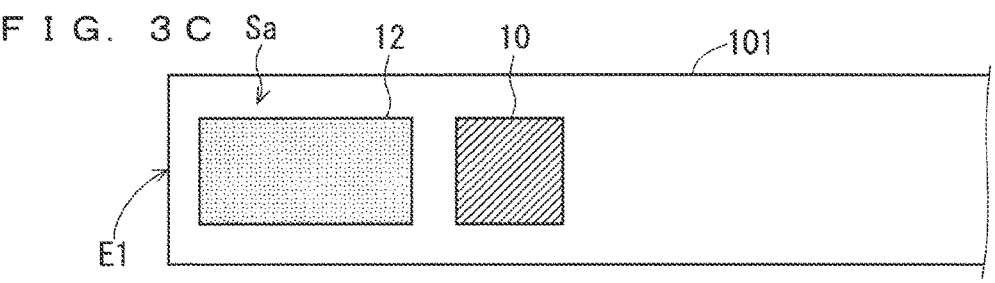
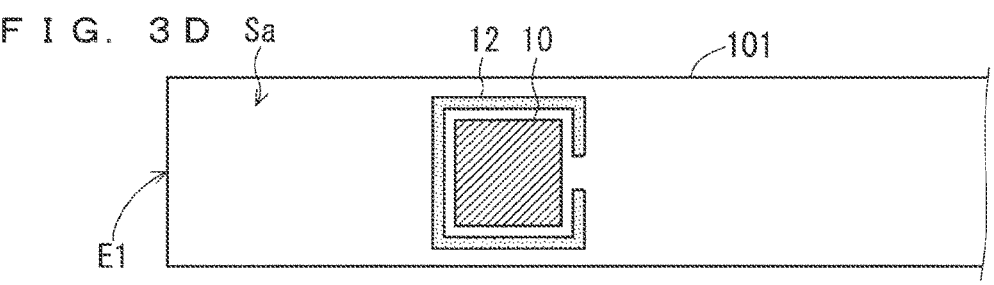
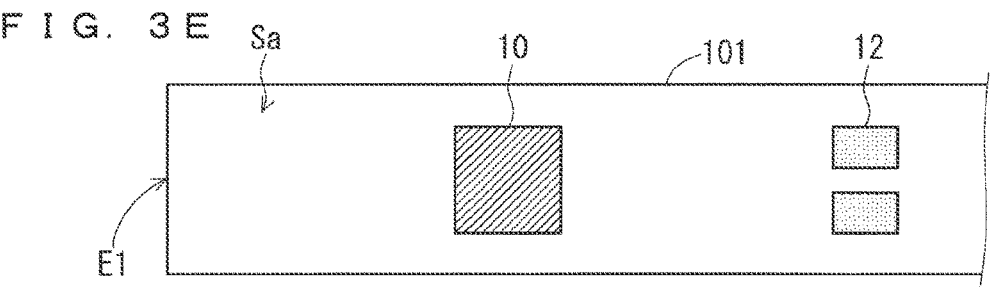

F I G . 4
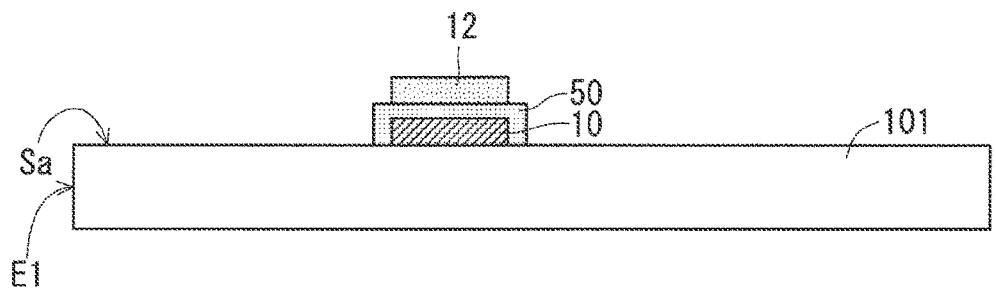
F I G . 5 A
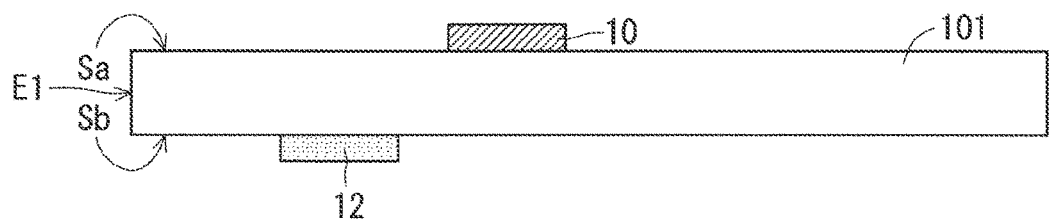
F I G . 5 B
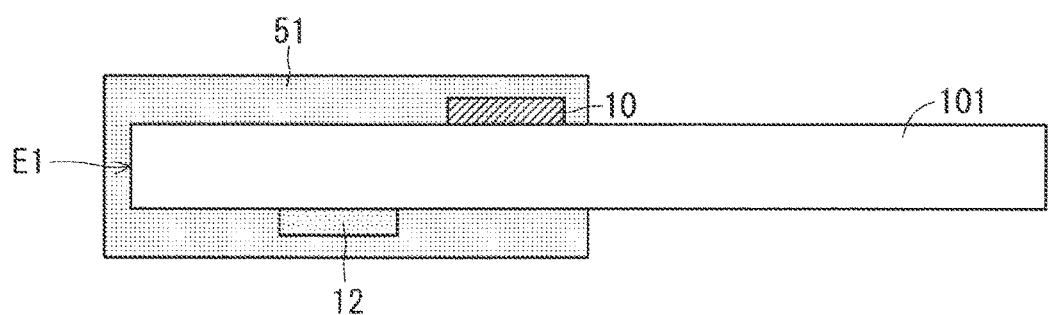

F I G. 7
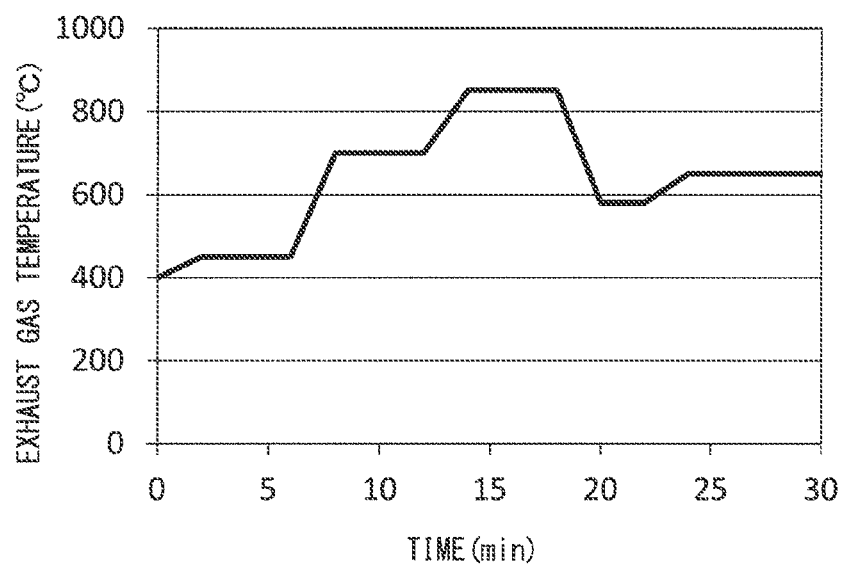

GAS SENSOR

BACKGROUND OF THE INVENTION

Field of the Invention

The present invention relates to a gas sensor for sensing a predetermined gas component in a measurement gas, and particularly relates to suppression of degradation of an electrode of the gas sensor.

Description of the Background Art

Conventionally widely known gas sensors are configured to sense a predetermined target gas component in a measurement gas, such as an exhaust gas from the engine of an automobile. Among such gas sensors, a gas sensor whose sensing electrode (measurement electrode) for sensing the target gas component includes a Pt—Au alloy have been publicly known (refer to Japanese Patent No. 4914447, Japanese Patent Application Laid-Open No. 2012-211928, and Japanese Patent No. 5883976, for example).

A large number of exhaust gas sensors each comprising a measurement electrode including a Pt—Au alloy have been disclosed.

For example, an exhaust gas from the engine of an automobile reaches at a high temperature of 900° C. approximately. When a conventionally known gas sensor whose sensing electrode formed of a Pt—Au alloy, as disclosed in Japanese Patent No. 4914447, Japanese Patent Application Laid-Open No. 2012-211928, and Japanese Patent No. 5883976, is used in an atmosphere at such a high temperature, there arises a problem that Au evaporates and the sensing electrode becomes Pt-riched because of the high temperature, which is not largely different from the melting point of Au (1064° C.). When the gas sensor is continuously used in such a high temperature atmosphere, its measurement accuracy degrades with time. Thus, each of the gas sensors disclosed in Japanese Patent No. 4914447, Japanese Patent Application Laid-Open No. 2012-211928, and Japanese Patent No. 5883976 has a problem that it has short product lifetime.

SUMMARY

The present invention relates to a gas sensor for sensing a predetermined gas component in a measurement gas, and is particularly directed to suppression of degradation of an electrode of the gas sensor.

According to the present invention, a gas sensor configured to measure a concentration of a predetermined gas component in a measurement gas includes: a sensor element mainly made of an oxygen-ion conductive solid electrolyte; at least one external electrode provided on the sensor element and containing a Pt—Au alloy; an electrode evaporation preventing film provided on the sensor element while being insulated from the sensor element and separated from the at least one external electrode, and made of Au or a Pt—Au alloy having an Au composition ratio not smaller than an Au composition ratio of the Pt—Au alloy contained in the at least one external electrode; and a protection cover provided so that at least part of the sensor element is positioned inside the protection cover and the measurement gas is introduced inside the protection cover, the at least one external electrode and the electrode evaporation preventing film being provided on the at least part of the sensor element.

The present invention achieves a gas sensor in which Au evaporation from a sensing electrode made of a Pt—Au alloy is suppressed so that degradation is unlikely to occur even when the gas sensor is continuously used under a high temperature atmosphere.

Thus, the present invention is intended to provide a gas sensor that is unlikely to have Au evaporation from an external electrode made of a Pt—Au alloy even when used under a high temperature atmosphere.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 1A and 1B are each sectional pattern diagrams schematically illustrating the configuration of a gas sensor 100 according to an exemplary preferred embodiment of the present invention;

FIGS. 3A, 3B, 3C, 3D, and 3E are diagrams exemplarily illustrating variations of the size, shape, and disposition of an electrode evaporation preventing film 12 in a sensor element 101;

FIG. 4 is a diagram exemplarily illustrating another different variation of the electrode evaporation preventing film 12;

FIGS. 5A and 5B are diagrams exemplarily illustrating other different variations of the electrode evaporation preventing film 12;

FIG. 7 is a diagram illustrating temporal change of an exhaust gas temperature in one cycle of operation of a gasoline engine used in an accelerated degradation test;

DESCRIPTION OF THE PREFERRED EMBODIMENTS

<Outline of Gas Sensor>

Figure 2A:
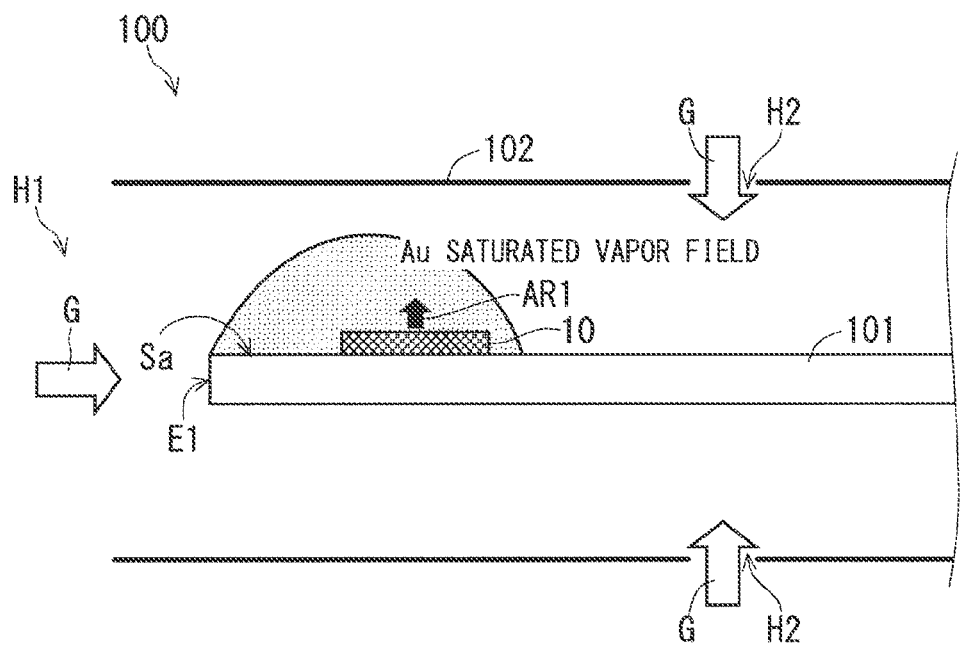
FIGS. 2A and 2B are each diagrams for description of suppression of Au evaporation from a sensing electrode 10.

FIGS. 1A and 1B are schematic sectional views schematically illustrating a configuration of a gas sensor 100 according to an exemplary preferred embodiment of the present invention. FIG. 1A is a vertical sectional view of a sensor element 101, which is a main component of the gas sensor 100, taken along the longitudinal direction of the sensor element 101. FIG. 1B is a view including a section vertical to the longitudinal direction of the sensor element 101 at position A-A' of FIG. 1A.

The gas sensor 100 is a so-called mixed-potential gas sensor. Generally speaking, the gas sensor 100 determines the concentration of a gas component, which is a measurement target, in a measurement gas using a potential difference that occurs between a sensing electrode 10, which is an external electrode provided on the surface of the sensor element 101 mainly made of ceramic that is an oxygen-ion conductive solid electrolyte such as zirconia ($ZrO_2$), and a reference electrode 20, which is provided inside the sensor element 101, due to a difference in the concentration of the gas component between the portions near the electrodes based on the principle of mixed potential.

More specifically, the gas sensor 100 preferably determines a target gas component in a measurement gas, where the measurement gas is an exhaust gas present in an exhaust pipe of an internal combustion engine such as a diesel engine or a gasoline engine. As the target gas component, a hydrocarbon (HC) gas, a carbon monoxide (CO) gas, and an ammonia ($NH_3$) gas are exemplified. Preferably, the gas sensor 100 is configured to excellently sense only a particular target gas component by changing the composition of the sensing electrode 10, the structure (for example, the porosity of a protective layer) or a control manner (for example, a temperature control manner) of the gas sensor 100 and the like.

The sensor element 101 mainly includes an insulating layer 11, an electrode evaporation protective film 12, a reference gas introduction layer 30, a reference gas introduction space 40, and a protective layer 50, in addition to the sensing electrode 10 and the reference electrode 20 described above.

In the present preferred embodiment, the sensor element 101 has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A and 1B. The sensor element 101 additionally includes other components mainly between these layers or on an outer peripheral surface of the element. The solid electrolytes constituting these six layers are fully airtight. Such a sensor element 101 is manufactured by, for example, laminating ceramic green sheets corresponding to the individual layers, which have been subjected to a predetermined process and printing of a circuit pattern, and further, by integrating the laminated layers through firing.

The gas sensor 100 does not necessarily need to include the sensor element 101 formed of such a laminated body including the six layers. The sensor element 101 may be formed as a laminated body having more or fewer layers or may not have a laminated structure.

In the following description, for convenience' sake, the surface located as the upper surface of the sixth solid electrolyte layer 6 in FIGS. 1A and 1B is referred to as a front surface Sa of the sensor element 101, and the surface located as the lower surface of the first solid electrolyte layer 1 in FIGS. 1A and 1B is referred to as a rear surface Sb of the sensor element 101. In the determination of the concentration of the target gas component in a measurement gas with the gas sensor 100, a predetermined range starting from a distal end E1 being one end of the sensor element 101, which includes at least the sensing electrode 10, is disposed in a measurement gas atmosphere; the other portion including a base end E2 opposite to the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view to have a thickness of 5 μm or more and 30 μm or less, at a position closer to the distal end E1 that is one end in the longitudinal direction of the sensor element 101 on the front surface Sa of the sensor element 101.

The gas sensor 100 is placed such that, in its use, at least the portion in which the sensing electrode 10 is provided is exposed to a measurement gas. In more detail, in the gas sensor 100, while a protection cover 102, which is not illustrated in FIGS. 1A and 1B (refer to FIGS. 2A and 2B), surrounds the sensor element 101, the protection cover 102 is provided with gas introduction holes (a distal end gas introduction hole H1 and a side gas introduction hole H2 (refer to FIGS. 2A and 2B)) for allowing the measurement gas to flow into and out of the protection cover 102, so that the sensing electrode 10 contacts the measurement gas in the protection cover 102.

The catalytic activity of the sensing electrode 10 against a target gas component is inactivated in a predetermined concentration range by suitably determining the composition of the Pt—Au alloy being its constituent material. That is, the decomposition reaction of the target gas component is prevented or reduced in the sensing electrode 10. Thus, in the gas sensor 100, the potential of the sensing electrode 10 selectively varies with respect to (has correlation with) the target gas component in the predetermined concentration range in accordance with the concentration thereof. In other words, the sensing electrode 10 is provided so as to have high concentration dependence of the potential for the target gas component in the predetermined concentration range while having low concentration dependence of the potential for other components of the measurement gas.

More specifically, in the sensor element 101 of the gas sensor according to the present preferred embodiment, with an Au abundance ratio on the surfaces of Pt—Au alloy particles included in the sensing electrode 10 being suitably determined, the sensing electrode 10 is provided so that the potential thereof has noticeable dependence on the concentration of the target gas component in a predetermined concentration range.

In this specification, the Au abundance ratio means an area ratio of a portion covered with Au to a portion at which Pt is exposed in the surface of noble metal particles included in the sensing electrode 10. In this specification, the Au abundance ratio is calculated from an expression shown below using Au and Pt detection values in an Auger spectrum obtained by performing Auger electron spectroscopy (AES) analysis on the surface of the noble metal particles.

$$\text{Au abundance ratio} = \text{Au detection value} / \text{Pt detection value} \quad (1)$$

The Au abundance ratio is one when the area of the portion at which Pt is exposed and the area of the portion covered with Au are equal to each other.

The Au abundance ratio can also be calculated using a relative sensitivity coefficient method from a peak intensity of a peak detected for Au and Pt, which is obtained by subjecting the surface of the noble metal particles to X-ray photoelectron spectroscopy (XPS) analysis. The value of the Au abundance ratio obtained by this method can be considered to be substantially the same as the value of the Au abundance ratio calculated based on the result of AES analysis.

The reference electrode 20 is an electrode having a substantially rectangular shape in plan view, which is provided inside the sensor element 101 and serves as a reference in the determination of the concentration of the measurement gas. The reference electrode 20 is provided as a porous cermet electrode of Pt and zirconia.

It suffices that the reference electrode 20 has a porosity of 10% or more and 30% or less and a thickness of 5 µm or more and 15 µm or less. The plane size of the reference electrode 20 may be smaller than that of the sensing electrode 10 as illustrated in FIGS. 1A and 1B, or may be equal to that of the sensing electrode 10.

The insulating layer 11 and the electrode evaporation preventing film 12 are laminated in this order on the surface Sa of the sensor element 101.

The insulating layer 11 is an underlayer of the electrode evaporation preventing film 12, which is formed of alumina and provided to electrically insulate the electrode evaporation preventing film 12 from any other part of the sensor element 101. It is not preferable to provide the electrode evaporation preventing film 12 in contact with the sixth solid electrolyte layer 6 without the insulating layer 11 because the electrode evaporation preventing film 12 would act as an electrode same as the sensing electrode 10. In addition, when being in contact with the sensing electrode 10, the electrode evaporation preventing film 12 would be an electrode integrated with the sensing electrode 10. To avoid this, the insulating layer 11 (and the electrode evaporation preventing film 12) is provided separately from the sensing electrode 10. The insulating layer 11 may have a thickness of 10 µm or more and 35 µm or less.

The electrode evaporation preventing film 12 is provided to prevent Au evaporation from the sensing electrode 10. The electrode evaporation preventing film 12 is formed of Au or a Pt—Au alloy that is Au-riched (has a large Au composition ratio) same as or more than the Pt—Au alloy constituting the sensing electrode 10, and is formed on the insulating layer 11. The electrode evaporation preventing film 12 has a plane shape substantially identical to that of the insulating layer 11 and a thickness of 5 µm or more and 30 µm or less.

Preferably, the Pt—Au alloy constituting the electrode evaporation preventing film 12 is more Au-riched than the Pt—Au alloy constituting in the sensing electrode 10 by 20 wt % or higher. In this case, Au evaporation from the sensing electrode 10 is more reliably prevented. The Au composition ratio of the Pt—Au alloy constituting the electrode evaporation preventing film 12, which is hereinafter simply referred to as an Au composition of the electrode evaporation preventing film 12, has an upper limit of 100 wt % when the electrode evaporation preventing film 12 is made of Au. Thus, in the present preferred embodiment, the description that the electrode evaporation preventing film 12 is formed of a Pt—Au alloy includes the case in which the electrode evaporation preventing film 12 is formed of Au only.

When the sensing electrode 10 and the electrode evaporation preventing film 12 are formed through screen printing and then integral firing (co-firing) of the solid electrolyte layers and the electrodes as described later, at least the Au composition of the electrode evaporation preventing film 12 is preferably 60 wt % or lower. When the Au composition is excessively large, the sensing electrode 10 and the electrode evaporation preventing film 12 melt during the firing because the melting point (1064° C.) of Au is lower than a firing temperature, which is not preferable. Since the electrode evaporation preventing film 12 has a composition same as that of the sensing electrode 10 or a composition more Au-riched than that of the sensing electrode 10 by 20 wt % or higher, the sensing electrode 10 is excellently formed when the composition of the electrode evaporation preventing film 12 is in a range of excellent formation.

In FIG. 1A, the electrode evaporation preventing film 12 (and the insulating layer 11) is provided at a position closer to the leading end part E1 by a predetermined distance than the sensing electrode 10 in an element longitudinal direction that is the horizontal direction in FIG. 1A, but this configuration is merely exemplary.

The electrode evaporation preventing film 12 will be described later in detail.

The reference gas introduction layer 30 is a layer made of porous alumina, which is provided inside the sensor element 101 to cover the reference electrode 20. The reference gas introduction space 40 is an internal space provided near the base end E2 of the sensor element 101. Air (oxygen), serving as a reference gas in the determination of the concentration of the target gas component, is externally introduced into the reference gas introduction space 40.

The reference gas introduction space 40 and the reference gas introduction layer 30 are in communication with each other, and accordingly, in the use of the gas sensor 100, the surrounding of the reference electrode 20 is always filled with air (oxygen) through the reference gas introduction space 40 and the reference gas introduction layer 30. During the use of the gas sensor 100, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even when the sensing electrode 10 is exposed to the measurement gas.

In the case illustrated in FIG. 1A, the reference gas introduction space 40 is provided in such a manner that part of the fifth solid electrolyte layer 5 is in communication with the exterior on the base end E2 of the sensor element 101. The reference gas introduction layer 30 is provided so as to extend in the longitudinal direction of the sensor element 101 between the fifth solid electrolyte layer 5 and the sixth solid electrolyte layer 6.

The protective layer 50 is a porous layer made of alumina being an insulating material, which is provided so as to cover at least the sensing electrode 10 on the front surface Sa of the sensor element 101. The protective layer 50 is provided as an electrode protective layer that prevents or reduces the degradation of the sensing electrode 10 due to continuous exposure to a measurement gas during the use of the gas sensor 100. In the case illustrated in FIG. 1A, the protective layer 50 is provided so as to cover not only the sensing electrode 10 but also the electrode evaporation preventing film 12 (and the insulating layer 11).

The protective layer 50 may be provided so as to have a thickness of 10 µm to 50 µm, and may have a pore size of 1 µm or less. The porosity of the protective layer 50 is preferably 5% or more and 40% or less. It is not preferable that the porosity is less than 5% because the measurement gas does not preferably arrive at the sensing electrode 10, and thus the responsiveness of the gas sensor 100 deteriorates. Such a porosity is not preferable also from the viewpoint that a formation of an Au saturated vapor field, as be described later, due to Au evaporation from the electrode evaporation preventing film 12 is prevented. It is not preferable that the porosity is more than 40% because a poisoning substance easily sticks to the sensing electrode 10 and the electrode evaporation preventing film 12, and thus a function of protecting the sensing electrode 10 and the electrode evaporation preventing film 12 cannot be sufficiently performed.

When the gas sensor 100 is used as an ammonia sensor, the protective layer 50 having the porosity of 40% or less also exhibits such an effect that influences of interference from other gas components can be suppressed, as described later.

In the present preferred embodiment, the porosity is evaluated by analyzing an enlarged cross-sectional SEM image (secondary electron image) (by referencing descriptions in Nobuyasu Mizutani et. al, "Ceramic Processing" (GIHODO SHUPPAN Co., Ltd.)).

As illustrated in FIG. 1B, the gas sensor 100 is equipped with a potentiometer 60 capable of measuring a potential difference between the sensing electrode 10 and the reference electrode 20. Although FIG. 1B schematically illustrates wiring of the sensing electrode 10, the reference electrode 20, and the potentiometer 60, in an actual sensor element 101, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The sensing electrode 10 and the reference electrode 20 are electrically connected with the potentiometer 60 through the wiring patterns and the connection terminals. Hereinafter, a potential difference between the sensing electrode 10 and the reference electrode 20, which is measured by the potentiometer 60, is also referred to as a sensor output.

The sensor element 101 further includes a heater part 70, which performs temperature control of heating the sensor element 101 and maintaining the temperature of the sensor element 101, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101 (in FIGS. 1A and 1B, the lower surface of the first solid electrolyte layer 1). The heater part 70 is electrically connected with an external power supply 80, so that it can be powered from the external power supply 80 through the heater electrode 71.

The heater 72 is an electric resistor provided inside the sensor element 101. The heater 72 is connected with the heater electrode 71 through the through hole 73 and generates heat by being powered externally via the heater electrode 71 to heat the solid electrolytes forming the sensor element 101 and maintain their temperatures.

In the case illustrated in FIGS. 1A and 1B, the heater 72 is buried while being vertically sandwiched between the second solid electrolyte layer 2 and the third solid electrolyte layer 3 so as to extend from the base end E2 to the position below the sensing electrode 10 near the distal end E1. The value of a voltage applied to the heater 72 by the external power source 80 is appropriately controlled by control means (not shown) to flow a heater current according to a desired temperature, thereby enabling the adjustment of the entire sensor element 101 to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth solid electrolyte layer 4 and to be in communication with the reference gas introduction space 40, and is formed to mitigate an internal pressure rise associated with a temperature rise in the heater insulating layer 74.

In the determination of the concentration of the target gas component in a measurement gas using the gas sensor 100 having such a configuration, as described above, air (oxygen) is supplied to the reference gas introduction space 40, with the sensor element 101 in only a predetermined range, which starts from the distal end E1 and includes at least the sensing electrode 10, being disposed in a space inside the protection cover 102 containing a measurement gas, and with the sensor element 101 on the base end E2 being apart from the space. The heater 72 heats the sensor element 101 to a predetermined temperature of 400° C. or higher and 800° C. or lower, which is set in accordance with the kind of the target gas component. The temperature of the sensor element 101 being heated by the heater 72 is also referred to as an element control temperature. In this preferred embodiment, the element control temperature is evaluated from the surface temperature of the sensing electrode 10. The surface temperature of the sensing electrode 10 can be evaluated by infrared thermography.

In a state described above, a potential difference occurs between the sensing electrode 10 exposed to the measurement gas and the reference electrode 20 exposed to the air. As described above, however, the potential of the reference electrode 20 disposed in the air (having a constant oxygen concentration) atmosphere is maintained at a constant potential, whereas the potential of the sensing electrode 10 selectively has a dependence on concentration for the target gas component in the measurement gas. The potential difference (sensor output) is thus substantially a value according to the composition of the measurement gas present around the sensing electrode 10. Therefore, a certain functional relationship (referred to as sensitivity characteristics) holds between the concentration of the target gas component and the sensor output. In the description below, such sensitivity characteristics may also be referred to as, for example, sensitivity characteristics for the sensing electrode 10.

In the actual determination of the concentration of the target gas component, in advance, a plurality of different mixed gases, each of which has a known concentration of the target gas component, are used as the measurement gas, and the sensitivity characteristics are experimentally identified by performing a measurement on the sensor output for each measurement gas. In the actual use of the gas sensor 100, accordingly, an operation processor (not shown) converts the sensor output, which varies from moment to moment in accordance with the concentration of the target gas component in a measurement gas, into the concentration of the target gas component based on the sensitivity characteristics. The concentration of the target gas component in the measurement gas can thus be determined almost in real time.

\<Suppression of Au Evaporation by Electrode Evaporation Preventing Film\>

Figure 2B:
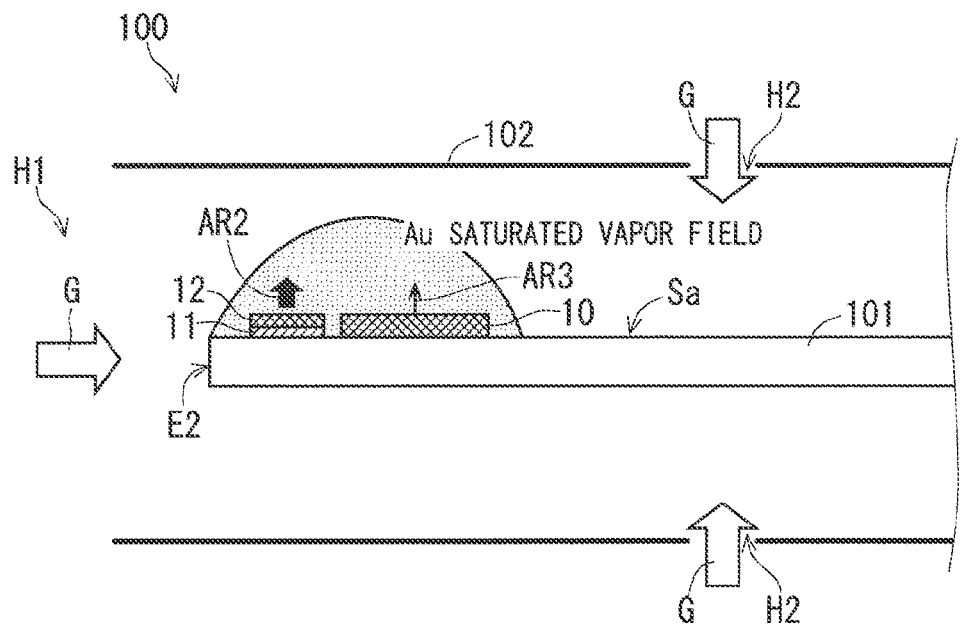

FIGS. 2A and 2B are each diagrams for description of suppression of Au evaporation from the sensing electrode 10, which is achieved by the electrode evaporation preventing film 12 included in the sensor element 101. FIG. 2A is a sectional pattern diagram in the case that the gas sensor 100 including no electrode evaporation preventing film 12 in the sensor element 101 is placed in a measurement gas atmosphere at high temperature (for example, 900° C. approximately). FIG. 2B is a sectional pattern diagram in the case that the gas sensor 100 according to the present preferred embodiment including the electrode evaporation preventing film 12 in the sensor element 101 is placed under the same condition. However, for simplification of description, the protective layer 50 is omitted in the illustrations. In each of the cases, the sensor element 101 itself is heated to the element control temperature of 400° C. or higher and 800° C. or lower by the heater 72 provided inside.

As illustrated in FIGS. 2A and 2B, in the gas sensor 100, the sensor element 101 is surrounded by the tubular (for example, cylindrical) protection cover 102. In FIGS. 2A and 2B, the protection cover 102 is provided with the distal end gas introduction hole H1 at a distal end part thereof, which is positioned further on the left side of the leading end part E1 of the sensor element 101 in FIGS. 2A and 2B, and the side gas introduction holes H2 at side thereof, which is positioned above and below the sensor element 101. These gas introduction holes allow a measurement gas G to flow into and out of the protection cover 102 therethrough.

The left side of the protection cover 102 is open for simplification of illustration in FIGS. 2A and 2B, but in reality, the protection cover 102 has a bottom, and the distal end gas introduction hole H1 is provided at part of the bottom. The side gas introduction holes H2 are typically provided at a plurality of places equally spaced from each other in the circumferential direction of the protection cover 102. In addition, the side gas introduction holes H2 may be provided at multiple stages in the longitudinal direction of the protection cover 102 (the horizontal direction in FIGS. 2A and 2B).

In the case that the sensor element 101 includes no electrode evaporation preventing film 12 as illustrated in FIG. 2A, Au evaporation indicated by arrow AR1 occurs from the sensing electrode 10 contacting the measurement gas G at high temperature, and an Au saturated vapor field is formed near the sensing electrode 10, whereas the composition of the sensing electrode 10 becomes Pt-riched. However, since the measurement gas G constantly flows into the protection cover 102 and continuously replaces an atmosphere inside the protection cover 102 little by little, the Au evaporation continuously occurs. Thus, the Au evaporation is not suppressed by formation of the Au saturated vapor field.

In the gas sensor 100 according to the present preferred embodiment illustrated in FIG. 2B, the measurement gas G at high temperature contacts not only the sensing electrode 10 but also the electrode evaporation preventing film 12. As described above, the electrode evaporation preventing film 12 is formed of the Pt—Au alloy having a composition same as or more Au-riched than that of the sensing electrode 10. Thus, in the gas sensor 100, Au evaporation occurs also from the electrode evaporation preventing film 12 as indicated by arrow AR2. The evaporation from the electrode evaporation preventing film 12 is more dominant than Au evaporation from the sensing electrode 10 indicated by arrow AR3 as the electrode evaporation preventing film 12 is more Au-riched.

In the gas sensor 100, too, an Au saturated vapor field is formed near the sensing electrode 10 due to the Au evaporation from the electrode evaporation preventing film 12 and the sensing electrode 10. However, unlike the case illustrated in FIG. 2A, Au evaporating from the electrode evaporation preventing film 12 contributes to formation of the Au saturated vapor field, and thus the Au evaporation from the sensing electrode 10 is suppressed as compared to the case illustrated in FIG. 2A. In other words, the Au evaporation from the sensing electrode 10 is suppressed by formation of the Au saturated vapor field through the Au evaporation from the electrode evaporation preventing film 12. In particular, as the electrode evaporation preventing film 12 is more Au-riched, the effect of the suppression is more significant.

The effect of the suppression of Au evaporation is checked by, for example, temporarily measuring the sensor output. Specifically, if Au evaporation is excellently suppressed, no temporal variation occurs to the sensor output as long as the concentration of the target gas component in the measurement gas is constant. However, if the Au evaporation proceeds, the sensor output decreases with time. Alternatively, whether the effect is achieved may be determined by performing an accelerated degradation test to check the effect and comparing the sensitivity characteristic before and after the test.

In the case that the sensor element 101 is provided with no protective layer 50, the effect can be checked by evaluating the Au abundance ratio at the surface of the sensing electrode 10 by a surface analysis method such as XPS.

Although the protective layer 50 is not illustrated in FIGS. 2A and 2B, also in the configuration in which the protective layer 50 is provided, the Au evaporation from the sensing electrode 10 and formation of the Au saturated vapor field occur if the sensor element 101 includes no electrode evaporation preventing film 12, but the Au evaporation from the sensing electrode 10 is suppressed if the sensor element 101 includes the electrode evaporation preventing film 12 since the Au evaporation from the electrode evaporation preventing film 12 contributes to formation of the Au saturated vapor field, as described above. In the case that the protective layer 50 is provided, the Au saturated vapor field is formed from the inside of pores in the protective layer 50 to the outside of the protective layer 50.

The above describes the mechanism of suppression of the Au evaporation from the sensing electrode 10 in the gas sensor 100 according to the present preferred embodiment, which is achieved by the sensor element 101 including the electrode evaporation preventing film 12.

\<Variation of Electrode Evaporation Preventing Film\>

FIGS. 3A, 3B, 3C, 3D, and 3E are diagrams exemplarily illustrating variations of the size, shape, and disposition of the electrode evaporation preventing film 12 in the sensor element 101. More specifically, FIGS. 3A, 3B, 3C, 3D, and 3E are top views of the sensor element 101, illustrating variations of the disposition of the electrode evaporation preventing film 12 when the sensing electrode 10 is disposed at the same position. The protective layer 50 is omitted in the illustrations. In any of these cases, the insulating layer 11 having a plane shape same as that of the electrode evaporation preventing film 12 is provided directly below the electrode evaporation preventing film 12.

FIGS. 3A, 3B, and 3C illustrate cases in which the electrode evaporation preventing film 12 having a rectangular shape in plan view is provided closer to the distal end part E1 in the element longitudinal direction than the sensing electrode 10 and has an area that is half, equal, and twice, respectively, the area of the sensing electrode 10. However, the electrode evaporation preventing film 12 is disposed at the same distance (in-plane distance) from the sensing electrode 10. FIG. 3B corresponds to the case exemplarily illustrated in FIGS. 1A and 1B. The in-plane distance means a shortest distance between the electrode evaporation preventing film 12 and the sensing electrode 10 in the plane of the sensor element 101. In other words, the in-plane distance is not the distance between the gravity centers of the electrode evaporation preventing film 12 and the sensing electrode 10.

FIG. 3D illustrates a case in which the electrode evaporation preventing film 12 surrounds the sensing electrode 10 in plan view. In the case illustrated in FIG. 3D, the in-plane distance between the electrode evaporation preventing film 12 and the sensing electrode 10, and the area ratio of the electrode evaporation preventing film 12 relative to the sensing electrode 10 are both smaller than those in the cases illustrated in FIGS. 3A, 3B, and 3C.

In the case illustrated in FIG. 3E, the electrode evaporation preventing film 12 having a rectangular shape in plan view and having an area same as that in the case illustrated in FIG. 3B is disposed on a side opposite to the distal end part E1 across the sensing electrode 10 (that is, a side closer to the base end part E2) in the element longitudinal direction, and the in-plane distance between the electrode evaporation preventing film 12 and the sensing electrode 10 is larger than that in the cases illustrated in FIGS. 3A, 3B, and 3C.

As illustrated in FIGS. 3A, 3B, 3C, 3D, and 3E, the area and shape of the electrode evaporation preventing film 12, the area ratio of the electrode evaporation preventing film 12 relative to the sensing electrode 10, and the in-plane distance between the electrode evaporation preventing film 12 and the sensing electrode 10 may differ and are not limited as long as the Au evaporation from the sensing electrode 10 is excellently suppressed. Although not illustrated, since the area of the sensing electrode 10 may differ in accordance with, for example, a characteristic required for the gas sensor 100, the area of the electrode evaporation preventing film 12 may be set accordingly as appropriate.

In any of the cases illustrated in FIGS. 3A, 3B, 3C, 3D, and 3E, the sensing electrode 10 and the electrode evaporation preventing film 12 are covered by the protective layer 50. The sensing electrode 10 and the electrode evaporation preventing film 12 may be covered by different protective layers 50, in the case that they are separated from each other with a relatively large in-plane distance therebetween as in the case illustrated in FIG. 3E, for example.

FIGS. 4, 5A, and 5B are diagrams exemplarily illustrating other different variations of the electrode evaporation preventing film 12. In FIGS. 5A and 5B, the insulating layer 11 is not illustrated. In reality, the insulating layer 11 is interposed between the sensor element 101 and the electrode evaporation preventing film 12.

In the sensor element 101 whose vertical cross-sectional view in the longitudinal direction is illustrated in FIG. 4, the electrode evaporation preventing film 12 is provided on the protective layer 50 covering the sensing electrode 10 to protect the sensing electrode 10. Thus, the in-plane distance between the electrode evaporation preventing film 12 and the sensing electrode 10 is zero in this case. The shortest distance between the electrode evaporation preventing film 12 and the sensing electrode 10 is equal to the thickness of the protective layer 50.

Also in the case illustrated in FIG. 4, the Au evaporation from the electrode evaporation preventing film 12 is more likely to occur than the Au evaporation from the sensing electrode 10, and the Au saturated vapor field is formed around the sensing electrode 10 mainly due to the Au evaporation from the electrode evaporation preventing film 12. The Au evaporation from the sensing electrode 10 is suppressed accordingly. The protective layer 50, which is made of alumina as an insulation material, serves as the insulating layer 11. In other words, the insulating layer 11 does not need to be formed in the case illustrated in FIG. 4.

Meanwhile, in the sensor element 101 whose vertical cross-sectional view in the longitudinal direction is illustrated in FIG. 5A, the electrode evaporation preventing film 12 is formed on the back surface Sb of the sensor element 101. Such a disposition is applicable. Also in this case, the area and shape of the electrode evaporation preventing film 12, the area ratio of the electrode evaporation preventing film 12 relative to the sensing electrode 10, and the in-plane distance between the electrode evaporation preventing film 12 and the sensing electrode 10 may be set as appropriate as long as the Au evaporation from the sensing electrode 10 is excellently suppressed by formation of the Au saturated vapor field mainly due to the Au evaporation from the electrode evaporation preventing film 12. Although no protective layer 50 is illustrated in FIG. 5A, the electrode evaporation preventing film 12 and the sensing electrode 10 may be covered by different protective layers 50 in this case.

Alternatively, as illustrated in FIG. 5B, the electrode evaporation preventing film 12 and the sensing electrode 10 may be collectively covered by a distal end protective film 51 provided at the distal end part E1 of the sensor element 101.

In FIGS. 1A and 1B, the sensing electrode 10 and the electrode evaporation preventing film 12 as external electrodes are provided on the surface Sa of the gas sensor 100, which is the upper surface of the sixth solid electrolyte layer 6. Alternatively, when an external electrode made of a Pt—Au alloy is provided on the back surface Sb or a side surface of the gas sensor 100, the electrode evaporation preventing film 12 may be provided in a corresponding manner to the external electrode.

<Process of Manufacturing Sensor Element>

The following describes a process of manufacturing the sensor element 101 using the configuration exemplarily illustrated in FIGS. 1A and 1B as an example. Generally speaking, the sensor element 101 as illustrated in FIGS. 1A and 1B is manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

Figure 6:
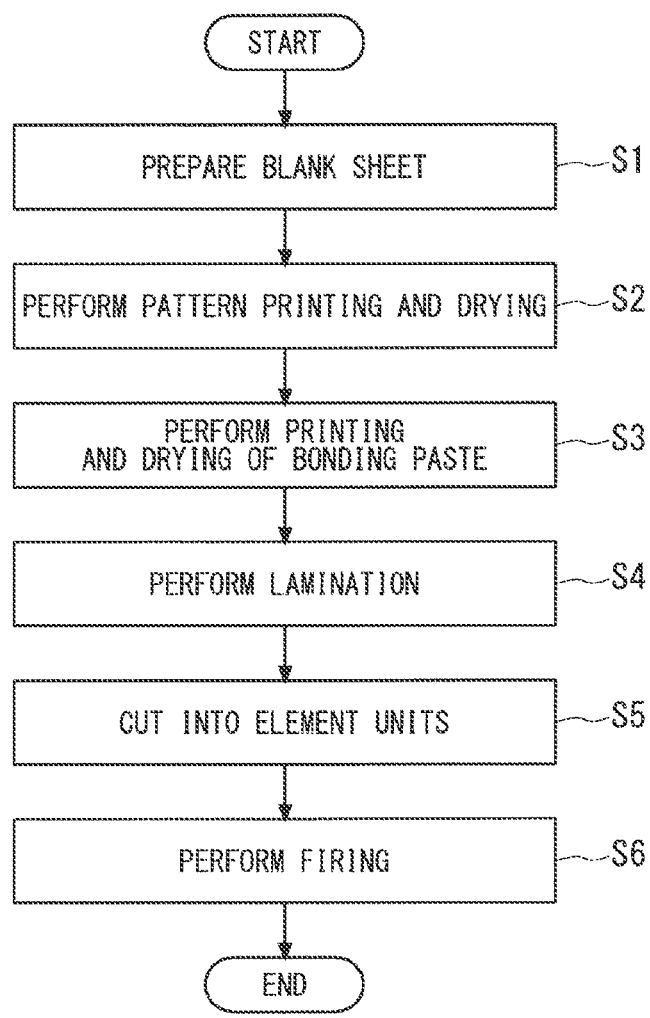
FIG. 6 is a diagram illustrating the process of processing of producing the sensor element 101.

FIG. 6 is a flowchart illustrating the process of manufacturing the sensor element 101. In the manufacture of the sensor elements 101A to 101C, first, blank sheets (not shown) that are green sheets having no pattern formed thereon are prepared (step S1). Specifically, six blank sheets corresponding to the first to sixth solid electrolyte layers 1 to 6 are prepared. A plurality of sheet holes used for positioning in printing and lamination are provided in the blank sheets. Such sheet holes are formed in advance through, for example, punching by a punching machine. For a green sheet whose corresponding layer forms an internal space, a penetration corresponding to the internal space is also provided in advance through, for example, punching as described above. All the blank sheets corresponding to the respective layers of the sensor element 101 need not to have the same thickness.

After the preparation of the blank sheets corresponding to the respective layers, pattern printing and drying are performed to form various patterns on the individual blank sheets (step S2). Specifically, electrode patterns for the sensing electrode 10, the reference electrode 20, and the like, patterns for the insulating layer 11 and the electrode evaporation preventing film 12, the reference gas introduction layer 30, patterns for the heater 72 and the heater insulating layer 74, and internal wiring (not shown) are formed. In this case, the patterns for the insulating layer 11 and the electrode evaporation preventing film 12 may be set in accordance with the various kinds of dispositions exemplarily illustrated in FIGS. 3A, 3B, 3C, 3D, 3E, 4, 5A, and 5B.

Each pattern is printed by applying a paste for pattern formation, prepared in accordance with the characteristic required for each formation target, to the blank sheet by a known screen printing technique. Any known drying means is available for drying after printing.

After the pattern printing, printing and drying of a bonding paste are performed to laminate and bond the green sheets corresponding to the respective layers (step S3). Any known screen printing technique is available for printing of a bonding paste, and any known drying means is available for drying after printing.

Subsequently, crimping is performed in which the adhesive-applied green sheets are laminated in a predetermined order, and the laminated green sheets are crimped on the predetermined temperature and pressure conditions, to thereby form a laminated body (step S4). Specifically, green sheets that are lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body has been obtained as described above, subsequently, a plurality of parts of the laminated body are cut out as individual units (referred to as element bodies) of the sensor element 101 (step S5). The cut out element bodies are fired under predetermined conditions, thereby producing the sensor element 101 as described above (step S6). In other words, the sensor element 101 is produced by co-firing the solid electrolyte layers and the electrodes. The firing temperature is preferably 1200° C. or higher and 1500° C. or lower (for example, 1400° C.). The integral firing performed in such a manner provides satisfactory adhesion strength to the respective electrodes of the sensor element 101.

The resultant sensor element 101 is housed in a predetermined housing and incorporated into main bodies (not shown) of the gas sensor 100. Subsequently, the protection cover 102 and any other component are attached, thereby to obtain the gas sensor 100.

As described above, the present preferred embodiment achieves a gas sensor in which Au evaporation from a sensing electrode made of a Pt—Au alloy is suppressed so that degradation is unlikely to occur even when the gas sensor is continuously used under a high temperature atmosphere.

<Modifications>

As described above, in the case that the electrode evaporation preventing film 12 made of a Pt—Au alloy is formed through screen printing and co-firing, the Au composition is preferably 60 wt % or lower due to the melting point of Au. However, if the electrode evaporation preventing film 12 is formed by other methods, the electrode evaporation preventing film 12 having an Au composition exceeding 60 wt % can be formed. Specifically, a method of manufacturing a laminated body and further the fired body therefrom without formation of the electrode evaporation preventing film 12, and then forming the electrode evaporation preventing film 12 with respect to the fired body is considered. For example, so-called secondary firing that is a method of forming the pattern of the electrode evaporation preventing film by screen printing and then performing firing again or a method of forming the electrode evaporation preventing film 12 by plating may be used.

In the above preferred embodiment, suppression of Au evaporation from an electrode provided on the surface of a sensor element in a mixed-potential type gas sensor is described as an example. However, the suppression of Au evaporation from an electrode by providing an electrode evaporation preventing film is applicable to a gas sensor of other type such as a limiting current type gas sensor (for example, an NOx sensor).

In the above-described preferred embodiment, the gas sensor 100 includes only the single sensing electrode 10 as an external electrode made of a Pt—Au alloy. However, the gas sensor 100 may include a plurality of such external electrodes. In this case, the electrode evaporation preventing film 12 may be provided individually for each external electrode, or the single electrode evaporation preventing film 12 may be provided to suppress Au evaporation from the external electrodes.

EXAMPLES

Example 1

Fabrication of the sensor element 101 was tried by forming the electrode evaporation preventing film 12 through screen printing and co-firing. Specifically, fabrication of a total of 15 of different sensor elements 101 (No. 1 to 15) was tried. In the sensor elements 101, the electrode evaporation preventing film 12 was disposed as in the cases illustrated in FIGS. 3A, 3B, and 3C with the Au composition ratio of the electrode evaporation preventing film 12 being set to five levels of 100 wt %, 60 wt %, 50 wt %, 30 wt %, and 10 wt %, and the area of the electrode evaporation preventing film 12 being set to three levels of 3.9 $mm^2$, 7.8 $mm^2$, and 15.6 $mm^2$. Formation of the protective layer 50 was omitted.

Each sensor element 101 had a length (size in the horizontal direction in FIG. 1A) of 97.5 mm, a width (size in the horizontal direction in FIG. 1B) of 4.25 mm, and a thickness (size in the vertical direction in FIGS. 1A and 1B) of 1.2 mm.

The sensing electrode 10 in each sensor element 101 had an Au composition of 10 wt % in a Pt—Au alloy and had a rectangular shape with an area of 7.8 $mm^2$ in plan view. The sensing electrode 10 was disposed at such a position that the center of gravity thereof is positioned at 8.0 mm from the distal end part E1. The distance between (in-plane distance) the electrode evaporation preventing film 12 and the sensing electrode 10 was constant at 0.46 mm between all sensor elements 101. The firing temperature for obtaining a fired body was 1400° C.

Table 1 lists, for each of the 15 sensor elements 101 (No. 1 to 15), main formation conditions of the electrode evaporation preventing film (simply referred to as an evaporation preventing film in Table 1 and the following tables), the ratio ("evaporation preventing film/sensing electrode area" ratio) of the area of the evaporation preventing film relative to the area of the sensing electrode, the number of a drawing illustrating exemplary arrangement of the sensing electrode and the electrode evaporation preventing film in the sensor element, and success or failure (success: circle, failure: cross) of co-firing. The success or failure of co-firing was determined by observing a section of each sensor element 101 obtained by the firing. Specifically, in the case that Au in the electrode evaporation preventing film 12 did not reach at the solid electrolyte through the penetration into the insulating layer 11, formation conditions of the sensor element 101 were determined to be conditions with which the electrode evaporation preventing film 12 can be formed by co-firing.

TABLE 1

| SENSOR NO. | EVAPORATION PREVENTING FILM Au COMPOSITION | EVAPORATION PREVENTING FILM AREA (mm²) | EVAPORATION PREVENTING FILM/SENSING ELECTRODE AREA RATIO | CORRESPONDING EXEMPLARY ARRANGEMENT | SUCCESS OR FAILURE OF CO-FIRING |
|---|---|---|---|---|---|
| 1 | 100 wt % | 3.9 | 0.5 | FIG. 3A | X |
| 2 |  | 7.8 | 1 | FIG. 3B | X |
| 3 |  | 15.6 | 2 | FIG. 3C | X |
| 4 | 60 wt % | 3.9 | 0.5 | FIG. 3A | ○ |
| 5 |  | 7.8 | 1 | FIG. 3B | ○ |
| 6 |  | 15.6 | 2 | FIG. 3C | ○ |
| 7 | 50 wt % | 3.9 | 0.5 | FIG. 3A | ○ |
| 8 |  | 7.8 | 1 | FIG. 3B | ○ |
| 9 |  | 15.6 | 2 | FIG. 3C | ○ |
| 10 | 30 wt % | 3.9 | 0.5 | FIG. 3A | ○ |
| 11 |  | 7.8 | 1 | FIG. 3B | ○ |
| 12 |  | 15.6 | 2 | FIG. 3C | ○ |
| 13 | 10 wt % | 3.9 | 0.5 | FIG. 3A | ○ |
| 14 |  | 7.8 | 1 | FIG. 3B | ○ |
| 15 |  | 15.6 | 2 | FIG. 3C | ○ |

As indicated in Table 1, the formation of the electrode evaporation preventing film 12 by co-firing was not successful for the sensor elements 101 of No. 1 to 3 in which the Au composition of the electrode evaporation preventing film 12 ratio was 100 wt %, but the electrode evaporation preventing film 12 was successfully formed in the sensor elements 101 of No. 4 to 15 having an Au composition ratio of 60 wt % or lower.

Example 2

The gas sensor 100 was assembled by using each of the sensor elements 101 of No. 4 to 15 in which it was confirmed that the electrode evaporation preventing film 12 was successfully formed in Example 1. The protection cover 102 has an inner diameter of 7.5 mm. An accelerated degradation test and evaluation of the sensitivity characteristics before and after the test were performed for each gas sensor 100 thus fabricated, and the level (evaporation prevention level) of Au evaporation suppress was evaluated by comparing those two sensitivity characteristics. As a comparative example, a gas sensor including no electrode evaporation preventing film 12 was fabricated, and the accelerated degradation test and evaluation of the evaporation prevention degree were performed.

The accelerated degradation test was performed in a manner that each gas sensor 100 was attached to an exhaust pipe of a gasoline engine (displacement: 1.8 L), and the gasoline engine was continuously operated for 60 hours under a periodic operating condition in a cycle of 30 minutes. The parameter λ was set to one. The element control temperature of the gas sensor 100 was set to 500° C.

FIG. 7 is a diagram illustrating temporal change of an exhaust gas temperature in one cycle of operation of the gasoline engine used in the accelerated degradation test. As understood from FIG. 7, the exhaust gas temperature periodically changed in the range of 400° C. to 850° C.

The evaluation of the sensitivity characteristic was performed with conditions below by using a plurality of kinds of model gasses containing a $C_2H_4$ gas having a known concentration as the target gas component (including a case with 0 ppm).

Element control temperature: 600° C.;
Gas atmosphere: $O_2$=10%;
$H_2O$=5%;
$C_2H_4$=0 ppm, 50 ppm, 70 ppm, 100 ppm, 200 ppm, 300 ppm, 500 ppm, 700 ppm, or 1000 ppm;
$N_2$=balance;
Gas flow rate: 5 L/min.

The evaporation prevention level was evaluated by determining whether the ratio of the sensor output after the accelerated degradation test relative to the sensor output before the accelerated degradation test was (A) 90% or higher, (B) 70% or higher (lower than 90%), or (C) lower than 70% when the concentration of $C_2H_4$ was 300 ppm.

To check the validity of the evaporation prevention level, a surface analysis by XPS was performed on the sensing electrode 10 and the electrode evaporation preventing film 12 (not in the comparative example) before and after the test for each of the gas sensors 100 of No. 4 to 6 and 13 to 15 and the gas sensor according to the comparative example to evaluate an Au ratio (Au/Au+Pt, unit: at %) in the Pt—Au alloy at each surface.

FIGS. 8 to 11 are diagrams illustrating the sensitivity characteristics obtained before and after the accelerated degradation test for the gas sensors 100 of No. 4 to 15 according to the present example and the gas sensor according to the comparative example. The sensitivity characteristics of the comparative example are illustrated in all of FIGS. 8 to 11.

Table 2 lists, for each of a total of 12 of the gas sensors 100 (No. 4 to 15) according to the present example and the gas sensor according to the comparative example, main formation conditions of the evaporation preventing film and the "evaporation preventing film/sensing electrode area" ratio (same as those listed in Table 1 except for the comparative example), a result of determination of the evaporation prevention level, and the Au ratios of the sensing electrode 10 and the electrode evaporation preventing film 12 before and after the test. In Table 2, the "Evaporation Prevention Level Determination" column has, based on the above-described determination, a double circle for (A), a circle for (B), and a cross for (C).

Au ratio at the surface of the electrode evaporation preventing film 12 was smaller after the test for any of the gas sensors 100 of No. 4 to 6.

On the other hand, for the gas sensors 100 of No. 13 to 15, the Au ratios at the surfaces of the sensing electrode 10 and the electrode evaporation preventing film 12 were smaller after the test. For the comparative example, the evaluation of the Au ratio at the surface of the sensing electrode 10 was tried only after the test, but no Au was detected.

Consideration on these Au ratio evaluation results and the above-described results of determination of the evaporation prevention level indicates that disposition of the electrode evaporation preventing film 12 having a composition at least

TABLE 2

| SENSOR NO. | EVAPORATION PREVENTING FILM | | EVAPORATION PREVENTING FILM/SENSING ELECTRODE AREA RATIO | EVAPORATION PREVENTION LEVEL DETERMINATION | Au RATIO OF SENSING ELECTRODE | | Au RATIO OF EVAPORATION PREVENTING FILM | |
|---|---|---|---|---|---|---|---|---|
| | Au COMPOSITION | AREA (mm$^2$) | | | BEFORE TEST | AFTER TEST | BEFORE TEST | AFTER TEST |
| 4 | 60 wt % | 3.9 | 0.5 | ◎ | 44 | 44 | 76 | 58 |
| 5 | | 7.8 | 1 | ◎ | 44 | 44 | 77 | 67 |
| 6 | | 15.6 | 2 | ◎ | 44 | 44 | 77 | 73 |
| 7 | 50 wt % | 3.9 | 0.5 | ◎ | | | | |
| 8 | | 7.8 | 1 | ◎ | | | | |
| 9 | | 15.6 | 2 | ◎ | | | | |
| 10 | 30 wt % | 3.9 | 0.5 | ◎ | | | | |
| 11 | | 7.8 | 1 | ◎ | | | | |
| 12 | | 15.6 | 2 | ◎ | | | | |
| 13 | 10 wt % | 3.9 | 0.5 | ○ | 44 | 28 | 44 | 28 |
| 14 | | 7.8 | 1 | ○ | 44 | 35 | 44 | 35 |
| 15 | | 15.6 | 2 | ○ | 44 | 39 | 44 | 39 |
| COMPARATIVE EXAMPLE | NO EVAPORATION PREVENTING FILM | | — | X | | 0 | | |

As for the comparative example, firstly, as understood from FIGS. 8 to 11, the sensitivity characteristic before the test was substantially equivalent to those of the gas sensors 100 of No. 4 to 15, but no sensitivity characteristic was obtained after the test. Accordingly, the gas sensor 100 according to the comparative example was determined to have an evaporation prevention level of lower than 70% as indicated in Table 2.

Figure 8:
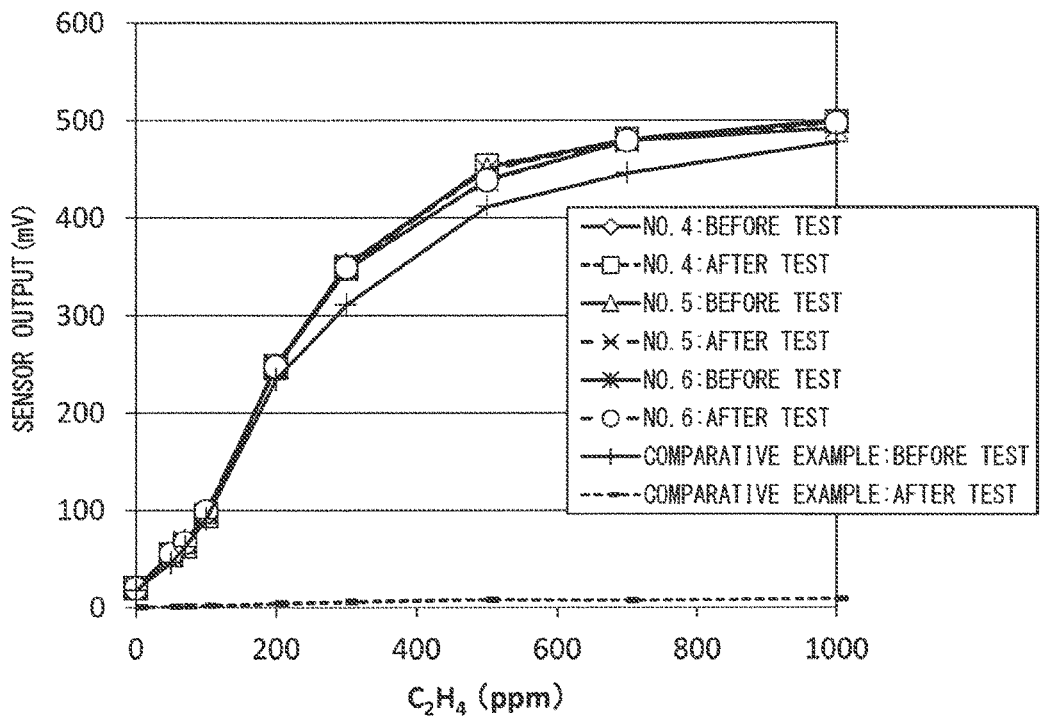
FIG. 8 is a diagram illustrating sensitivity characteristics obtained before and after the accelerated degradation test for the gas sensors 100 according to Example 2 and a gas sensor according to a comparative example.
Figure 9:
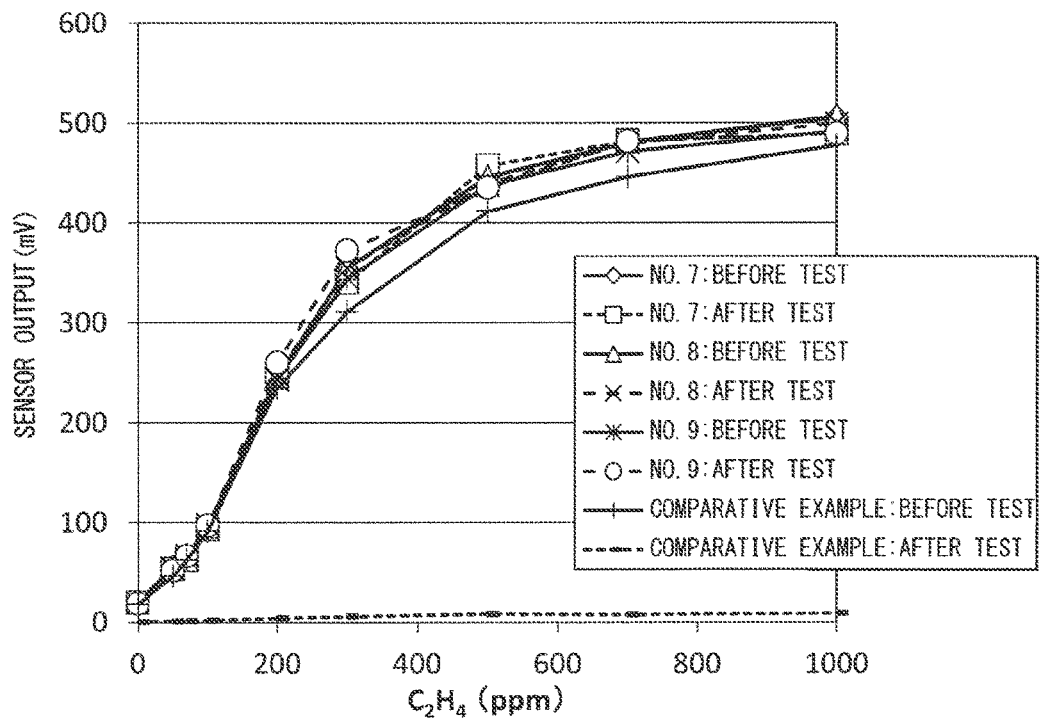
FIGS. 9, 10, and 11 are diagrams illustrating sensitivity characteristics obtained before and after the accelerated degradation test for the gas sensors 100 according to Example 2 and the gas sensor according to the comparative example.
Figure 10:
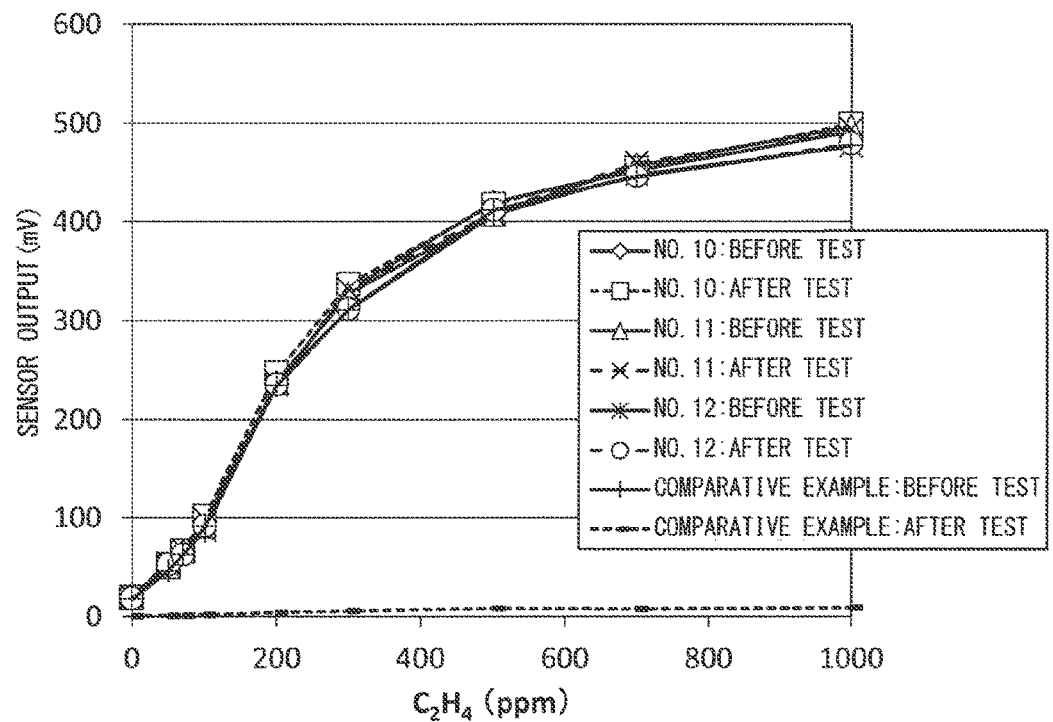

However, as understood from FIGS. 8 to 10, the gas sensors 100 of No. 4 to 12 in which the electrode evaporation preventing film 12 had an Au composition of 30 wt % or higher, which is larger than the Au composition of 10 wt % of the sensing electrode 10 by 20 wt % or more, had almost no difference in the sensitivity characteristic before and after the accelerated degradation test. As indicated in Table 2, these gas sensors 100 were each determined to have an evaporation prevention level of 90% or higher.

Figure 11:
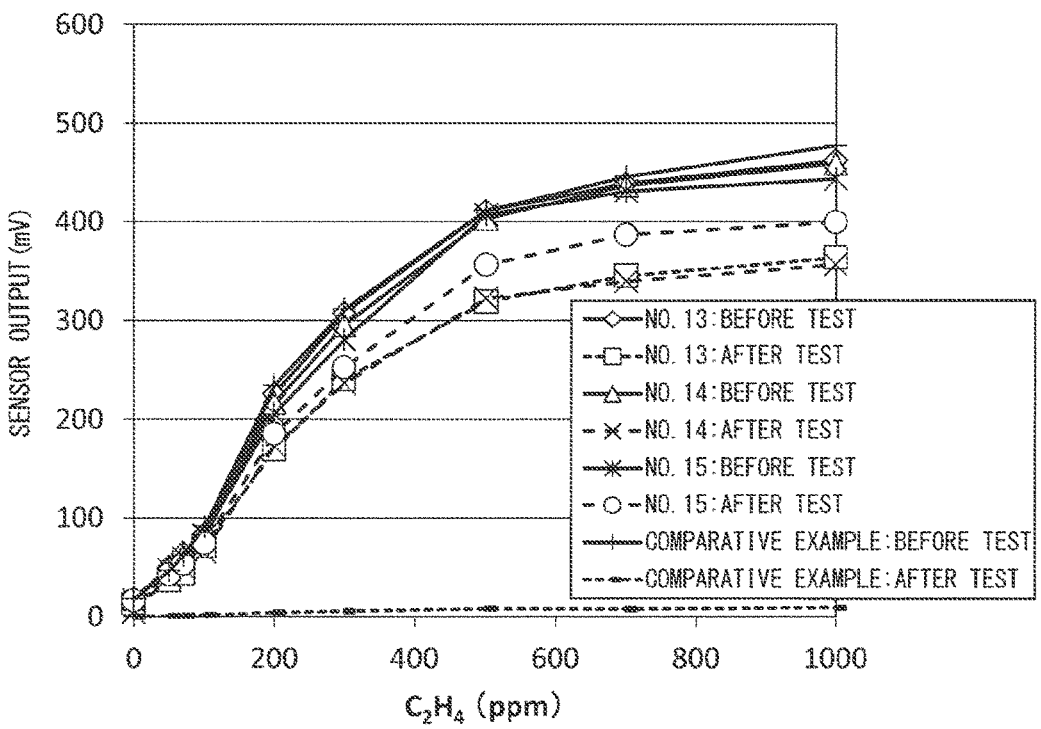

For the gas sensors 100 of No. 13 to 15 illustrated in FIG. 11 in which the electrode evaporation preventing film 12 had an Au composition same as that of the sensing electrode 10, the sensitivity characteristic after the test degraded somehow as compared to the sensitivity characteristic before the test. However, as indicated in Table 2, these gas sensors 100 were each determined to have an evaporation prevention level of 70% or higher.

As for the Au ratios of the sensing electrode 10 and the electrode evaporation preventing film 12, the Au ratio of the surface of the sensing electrode 10 had no change before and after the test for the gas sensors 100 of No. 4 to 6, which were determined to have an evaporation prevention level of 90% or higher. In other words, the Au evaporation from the sensing electrode 10 was completely suppressed. Only the same as or more Au-riched than that of the sensing electrode 10 facilitates suppression of the Au evaporation from the sensing electrode 10. In addition, there is a correspondence relation between the magnitude of the evaporation prevention level and change in the Au ratio of the sensing electrode 10. This indicates that it is appropriate to evaluate the degree of Au evaporation suppression based on the evaporation prevention level.

It is also indicated that, when having an area half of that of the sensing electrode 10, the electrode evaporation preventing film 12 sufficiently provides the Au evaporation suppression effect.

Example 3

The four gas sensors 100 (No. 16 to 19) were fabricated as in Examples 1 and 2 except that the sensing electrode 10 and the electrode evaporation preventing film 12 in each sensor element 101 are arranged differently from those in Example 2. For each gas sensor 100 thus fabricated, the evaporation prevention level was evaluated by performing the accelerated degradation test and the evaluation of the sensitivity characteristic before and after the test, as in Example 2.

Specifically, the two gas sensors 100 (No. 16 and 17) were fabricated. In these two gas sensors 100, as in the gas sensor 100 of No. 8 in Examples 1 and 2, the sensing electrode 10 having an Au composition of 10 wt % and the electrode evaporation preventing film 12 having an Au composition of 50 wt % were provided in rectangular shapes with the same area in plan view as illustrated in FIG. 3B, and had an in-plane distance of 0.46 mm therebetween, which is same as that of the gas sensor 100 of No. 8, and the area was 0.4 mm² and 3 mm², respectively, which are smaller than that of the gas sensor 100 of No. 8.

In addition, the two gas sensors 100 (No. 18 and 19) were fabricated. In these two gas sensors 100, the sensing electrode 10 and the electrode evaporation preventing film 12 had Au compositions same as those of the gas sensors of No. 8, 16, and 17, the area was 3 mm², which is same as that of the gas sensor 100 of No. 17, the sensing electrode 10 was provided in a rectangular shape in plan view, and the electrode evaporation preventing film 12 was disposed as illustrated in FIGS. 3D and 3E. The in-plane distance of the sensing electrode 10 and the electrode evaporation preventing film 12 was 0.15 mm and 4.5 mm in the gas sensors 100 of No. 18 and 19, respectively. In the gas sensor 100 of No. 19, the electrode evaporation preventing film 12 was disposed at a threshold disposition position at the base end E2, where it is difficult to further separate the electrode evaporation preventing film 12 from the sensing electrode 10 because of contact with any other member due to the structure of the gas sensor 100.

Also in this fabrication of the gas sensors 100 of No. 16 to 19, the electrode evaporation preventing film 12 was successfully formed through screen printing and co-firing.

Figure 12:
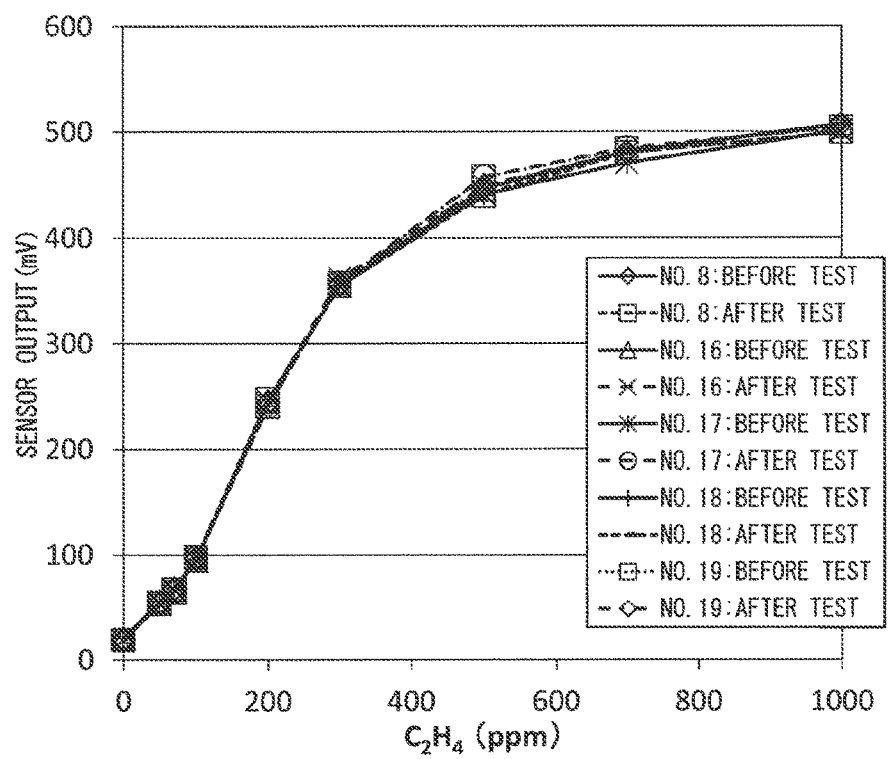
FIG. 12 is a diagram illustrating sensitivity characteristics obtained before and after the accelerated degradation test for the gas sensors 100 according to Example 3 and the gas sensor 100 of No. 8.

FIG. 12 is a diagram illustrating the sensitivity characteristics obtained before and after the accelerated degradation test for the four gas sensors 100 (No. 16 to 19) according to the present example and the gas sensor 100 of No. 8 for comparison.

Table 3 lists, for the gas sensors 100 (No. 16 to 19) according to the present example and the gas sensor 100 of No. 8 for comparison, the areas of the sensing electrode 10 and the electrode evaporation preventing film 12, the in-plane distance therebetween, the number of a drawing illustrating exemplary arrangement of the sensing electrode and the electrode evaporation preventing film, and a result of determination of the evaporation prevention level.

vided, the Au evaporation suppression effect can be obtained up to at least a position separated from the sensing electrode 10 by 4.5 mm.

Example 4

The gas sensor 100 was fabricated as in Examples 1 to 3 except that the protective layer 50 was provided to the sensor element 101 and the electrode evaporation preventing film 12 was disposed in a different relation with the protective layer 50. For each gas sensor 100 thus fabricated, the evaporation prevention level was evaluated by performing the accelerated degradation test and the evaluation of the sensitivity characteristic before and after the test, as in Examples 2 and 3.

Specifically, the sensing electrode 10 and the electrode evaporation preventing film 12 had Au compositions and an area same as those of the gas sensor 100 of No. 8 in Examples 1 and 2. Specifically, the Au compositions, the area, and the in-plane distance were 10 wt %, 50 wt %, 7.8 mm², and 0.46 mm, respectively.

The protective layer 50 was formed with the porosity being set to three levels of 12%, 20%, 40% and the thickness being set to two levels of 15 μm and 30 μm. The electrode evaporation preventing film 12 was disposed in two manners. In one of the dispositions, as exemplarily illustrated in FIG. 4, the electrode evaporation preventing film 12 was exposed on the protective layer 50 formed to cover the sensing electrode 10. In the other disposition, as exemplarily illustrated in FIG. 3B, the electrode evaporation preventing film 12 was disposed similarly to the gas sensor 100 of No. 8 and covered by the protective layer 50 together with the sensing electrode 10 as illustrated in FIGS. 1A and 1B. In the former disposition, the sensing electrode 10 and the electrode evaporation preventing film 12 were provided above and below the protective layer 50 in FIG. 4 but had an

TABLE 3

| SENSOR NO. | AREAS OF SENSING ELECTRODE AND EVAPORATION PREVENTING FILM (mm²) | IN-PLANE DISTANCE BETWEEN SENSING ELECTRODE AND EVAPORATION PREVENTING FILM (mm) | CORRESPONDING EXEMPLARY ARRANGEMENT | EVAPORATION PREVENTION LEVEL DETERMINATION |
|---|---|---|---|---|
| 16 | 0.4 | 0.46 | FIG. 3B | ◎ |
| 17 | 3 | 0.46 | FIG. 3B | ◎ |
| 8 | 7.8 | 0.46 | FIG. 3B | ◎ |
| 18 | 3 | 0.15 | FIG. 3D | ◎ |
| 19 | 3 | 4.5 | FIG. 3E | ◎ |

As understood from FIG. 12, the sensitivity characteristic had almost no difference before and after the accelerated degradation test for all gas sensors 100 including the gas sensor 100 of No. 8. Accordingly, as indicated in Table 3, any of the gas sensors 100 was determined to have an evaporation prevention level of 90% or higher.

This result indicates that the Au evaporation can be suppressed when the electrode evaporation preventing film 12 having an area in accordance with that of the sensing electrode 10 is provided, and also even when the electrode evaporation preventing film 12 has different shapes and is disposed at different positions. According to a result on the gas sensor 100 of No. 19, in particular, it is understood that, when the electrode evaporation preventing film 12 is proin-plane distance of 0 mm. In the latter disposition, the in-plane distance was 4.6 mm, which was same as that in the gas sensor of No. 8.

In the above-described manner, the 12 gas sensors 100 (No. 20 to 31) were fabricated. Also in this fabrication of the gas sensors 100 of No. 20 to 31, the electrode evaporation preventing film 12 was successfully formed through screen printing and co-firing.

Figure 13:
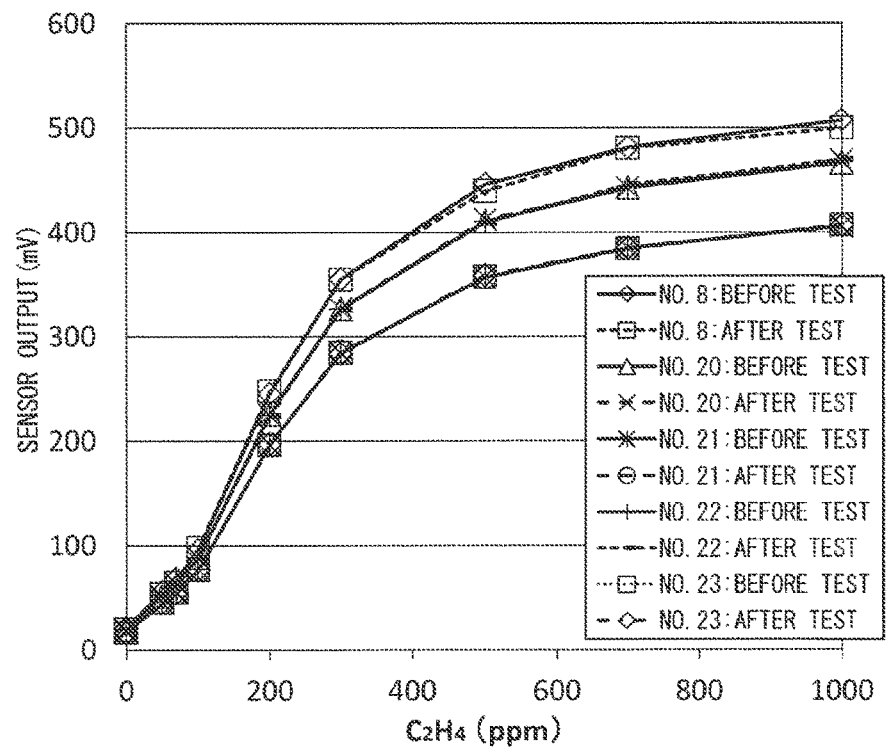
FIGS. 13, 14, and 15 are diagrams illustrating sensitivity characteristics obtained before and after the accelerated degradation test for the gas sensors 100 according to Example 4 and the gas sensor 100 of No. 8.
Figure 14:
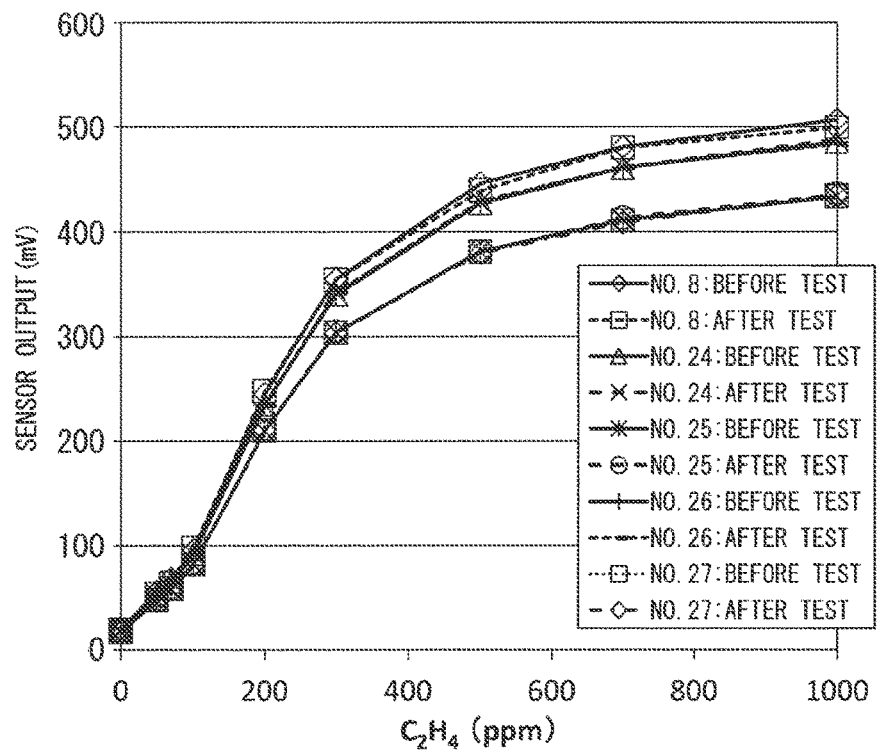
Figure 15:
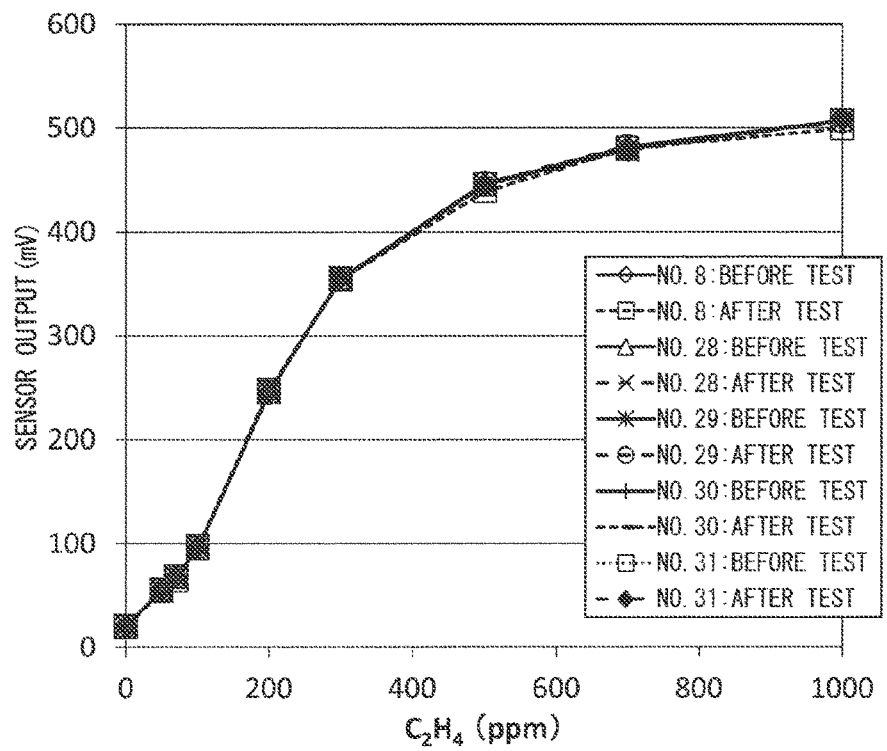

FIGS. 13 to 15 are diagrams illustrating the sensitivity characteristics obtained before and after the accelerated degradation test for the gas sensors 100 of No. 20 to 31 according to the present example and the gas sensor 100 of No. 8 for comparison. The sensitivity characteristics for the gas sensor 100 of No. 8 are illustrated in all of FIGS. 13 to 15.

Table 4 lists, for the gas sensors 100 (No. 20 to 31) according to the present example and the gas sensor 100 of No. 8 for comparison, main formation conditions (porosity and thickness) of the protective layer, disposition of the electrode evaporation preventing film 12, the in-plane distance of the sensing electrode 10 and the electrode evaporation preventing film 12, and a result of determination of the evaporation prevention level.

TABLE 4

| SENSOR NO. | PROTECTIVE LAYER POROSITY (%) | PROTECTIVE LAYER THICKNESS (μm) | DISPOSITION OF EVAPORATION PREVENTING FILM | IN-PLANE DISTANCE BETWEEN SENSING ELECTRODE AND EVAPORATION PREVENTING FILM (mm) | EVAPORATION PREVENTION LEVEL DETERMINATION |
|---|---|---|---|---|---|
| 20 | 12 | 15 | EXPOSED ON PROTECTIVE LAYER | 0 | ⊚ |
| 21 |  | 30 | EXPOSED ON PROTECTIVE LAYER | 0 | ⊚ |
| 22 |  | 15 | COVERED BY PROTECTIVE LAYER | 0.46 | ⊚ |
| 23 |  | 30 | COVERED BY PROTECTIVE LAYER | 0.46 | ⊚ |
| 24 | 20 | 15 | EXPOSED ON PROTECTIVE LAYER | 0 | ⊚ |
| 25 |  | 30 | EXPOSED ON PROTECTIVE LAYER | 0 | ⊚ |
| 26 |  | 15 | COVERED BY PROTECTIVE LAYER | 0.46 | ⊚ |
| 27 |  | 30 | COVERED BY PROTECTIVE LAYER | 0.46 | ⊚ |
| 28 | 40 | 15 | EXPOSED ON PROTECTIVE LAYER | 0 | ⊚ |
| 29 |  | 30 | EXPOSED ON PROTECTIVE LAYER | 0 | ⊚ |
| 30 |  | 15 | COVERED BY PROTECTIVE LAYER | 0.46 | ⊚ |
| 31 |  | 30 | COVERED BY PROTECTIVE LAYER | 0.46 | ⊚ |
| 8 | NO PROTECTIVE LAYER | | EXPOSED | 0.46 | ⊚ |

As understood from FIGS. 13 to 15, the sensitivity characteristic had almost no difference before and after the accelerated degradation test for any of the gas sensors 100 including the gas sensor 100 of No. 8. Thus, as indicated in Table 4, any of the gas sensors 100 was determined to have an evaporation prevention level of 90% or higher.

However, there was a difference in the sensitivity characteristics among these gas sensors. The gas sensors of No. 28 to 31 illustrated in FIG. 15 in which the protective layer 50 had a porosity of 40% had sensitivity characteristics similarly to that of the gas sensor 100 of No. 8 including no protective layer 50. The gas sensors of No. 20 to 23 illustrated in FIG. 13 in which the protective layer 50 had a porosity of 12% and the gas sensors 100 of No. 24 to 27 illustrated in FIG. 14 in which the protective layer 50 had a porosity of 20% had slightly degraded sensitivity characteristics as compared to that of the gas sensor 100 of No. 8. In more detail, the sensitivity characteristics obtained for the gas sensors 100 (No. 20 and 24), in which the protective layer 50 had a thickness of 15 μm and the electrode evaporation preventing film 12 was provided on the protective layer 50, were closer to those for the gas sensor 100 of No. 8 than those of the other gas sensors. Like the case illustrated in FIG. 15, more excellent sensitivity characteristic is obtained for a larger porosity of the protective layer 50 if the other conditions are same.

The above-described results indicate that, as long as formation conditions of the protective layer 50 and disposition of the electrode evaporation preventing film 12 are appropriate, the protective layer 50 does not hinder the Au evaporation suppression effect, and thus the formation conditions of the protective layer 50 can be set in accordance with a desired sensitivity characteristic.

While the invention has been shown and described in detail, the foregoing description is in all aspects illustrative and not restrictive. It is therefore understood that numerous modifications and variations can be devised without departing from the scope of the invention.

What is claimed is:

1. A gas sensor for measuring a concentration of a predetermined gas component in a measurement gas, comprising:
   a sensor element mainly made of an oxygen-ion conductive solid electrolyte;
   at least one external electrode provided on said sensor element and containing a Pt—Au alloy;
   an insulating layer formed on said sensor element and separated from said at least one external electrode;
   an electrode evaporation preventing film laminated on said insulating layer and separated from said at least one external electrode, and made of Au or a Pt—Au alloy having an Au composition ratio not smaller than an Au composition ratio of the Pt—Au alloy contained in said at least one external electrode; and
   a protection cover provided so that at least part of said sensor element is positioned inside said protection cover and said measurement gas is introduced inside said protection cover, said at least one external electrode and said electrode evaporation preventing film being provided on said at least part of said sensor element.

2. The gas sensor according to claim 1, wherein said electrode evaporation preventing film is made of Au or a Pt—Au alloy having an Au composition ratio larger than the Au composition ratio of said at least one external electrode by 20 wt. % or more.

3. The gas sensor according to claim 1, wherein said insulating layer and said at least one external electrode are formed on an identical surface of said sensor element.

4. The gas sensor according to claim 3, further comprising an insulating porous protective layer covering said electrode evaporation preventing film and said at least one external electrode.

5. The gas sensor according to claim 1, further comprising a porous protective layer covering said at least one external electrode, wherein said electrode evaporation preventing film is laminated on said protective layer.

6. The gas sensor according to claim 1, further including:
   a reference electrode is formed of a cermet of Pt and an oxygen-ion conductive solid electrolyte, said at least one external electrode is a sensing electrode formed of a cermet of a Pt—Au alloy and an oxygen-ion conductive solid electrolyte, and said gas sensor is configured to determine the concentration of said predetermined gas component based on a potential difference between said sensing electrode and said reference electrode.

7. The gas sensor according to claim 2, further including:

a reference electrode is formed of a cermet of Pt and an oxygen-ion conductive solid electrolyte, said at least one external electrode is a sensing electrode formed of a cermet of a Pt—Au alloy and an oxygen-ion conductive solid electrolyte, and said gas sensor is configured to determine the concentration of said predetermined gas component based on a potential difference between said sensing electrode and said reference electrode.

8. The gas sensor according to claim 3, further including:

a reference electrode is formed of a cermet of Pt and an oxygen-ion conductive solid electrolyte, said at least one external electrode is a sensing electrode formed of a cermet of a Pt—Au alloy and an oxygen-ion conductive solid electrolyte, and said gas sensor is configured to determine the concentration of said predetermined gas component based on a potential difference between said sensing electrode and said reference electrode.

9. The gas sensor according to claim 4, further including:

a reference electrode is formed of a cermet of Pt and an oxygen-ion conductive solid electrolyte, said at least one external electrode is a sensing electrode formed of a cermet of a Pt—Au alloy and an oxygen-ion conductive solid electrolyte, and said gas sensor is configured to determine the concentration of said predetermined gas component based on a potential difference between said sensing electrode and said reference electrode.

10. The gas sensor according to claim 5, further including:

a reference electrode is formed of a cermet of Pt and an oxygen-ion conductive solid electrolyte, said at least one external electrode is a sensing electrode formed of a cermet of a Pt—Au alloy and an oxygen-ion conductive solid electrolyte, and said gas sensor is configured to determine the concentration of said predetermined gas component based on a potential difference between said sensing electrode and said reference electrode.

* * * * *